United States Patent [19]
McDonnell et al.

[11] Patent Number: 5,591,184
[45] Date of Patent: Jan. 7, 1997

[54] FLUID JET SURGICAL CUTTING INSTRUMENT

[75] Inventors: Christopher McDonnell, Newtown; David L. Cortez, Brookfield; Kenneth H. Whitfield, New Haven; Ian M. Scott, Ridgefield, all of Conn.

[73] Assignee: Sentinel Medical, Inc., Norcross, Ga.

[21] Appl. No.: 322,882

[22] Filed: Oct. 13, 1994

[51] Int. Cl.⁶ .................................. A61B 17/32
[52] U.S. Cl. ................... 606/167; 606/160; 606/159; 604/22
[58] Field of Search ................... 606/159, 107, 606/170; 604/22, 30, 31, 151, 152, 153, 247, 38; 628/DIG. 10, DIG. 12

[56] References Cited

U.S. PATENT DOCUMENTS

| | | |
|---|---|---|
| 1,889,425 | 11/1932 | Sorensen . |
| 3,590,813 | 7/1971 | Roszyk . |
| 3,811,795 | 5/1974 | Olsen . |
| 3,930,505 | 1/1976 | Wallach . |
| 3,993,054 | 11/1976 | Newman . |
| 4,024,966 | 5/1977 | Wallach . |
| 4,186,733 | 2/1980 | Mogaki . |
| 4,368,734 | 1/1983 | Banko . |
| 4,441,488 | 4/1984 | Macabee . |
| 4,690,672 | 9/1987 | Veltrup . |
| 4,694,828 | 9/1987 | Eichenbaum . |
| 4,935,006 | 6/1990 | Hasson . |
| 4,944,726 | 7/1990 | Hillal et al. . |
| 5,024,615 | 6/1991 | Buchel . |
| 5,037,431 | 8/1991 | Summers et al. . |
| 5,135,482 | 8/1992 | Neracher . |
| 5,261,883 | 11/1993 | Hood et al. . |
| 5,361,583 | 11/1994 | Huitema . |
| 5,370,609 | 12/1994 | Drasler et al. ............ 606/159 |

FOREIGN PATENT DOCUMENTS

| | | |
|---|---|---|
| 0175096A1 | 3/1986 | European Pat. Off. . |
| 0258901A2 | 3/1988 | European Pat. Off. . |
| 0411170A1 | 2/1991 | European Pat. Off. . |
| 0447718A1 | 9/1991 | European Pat. Off. . |
| 0555549A1 | 8/1993 | European Pat. Off. . |

OTHER PUBLICATIONS

*Transection of the Liver With a Water Jet*, Bo G. Persson et al., Surgery Gynecology & Obstetrics (Mar. 1989), pp. 267, 268.
*Rheolytic Catheter for Percutaneous Removal of Thrombus*, William J. Drasler et al., Radiology, pp. 263–267.
*A Critical Examination of the Use of Water Jets for Medical Applications*, M. M. Vijay, 5th American Water Jet Conference (1989).

Primary Examiner—Michael Powell Buiz
Assistant Examiner—William Lewis
Attorney, Agent, or Firm—Harris Zimmerman

[57] ABSTRACT

A fluid jet surgical cutting instrument having a pressure generating mechanism disposed within the housing of the instrument. The pressure generating mechanism includes a piston member which is reciprocatingly movable within the housing by alternately supplying gas to the distal end of the piston and the proximal end of the piston. The gas is supplied in an alternating manner through the provision of a novel actuator mechanism which includes a plurality of passageways which permits charging of gas to the pressure amplifying mechanism as well as venting of gas from the pressure amplifying mechanism to permit reciprocating movement.

23 Claims, 10 Drawing Sheets

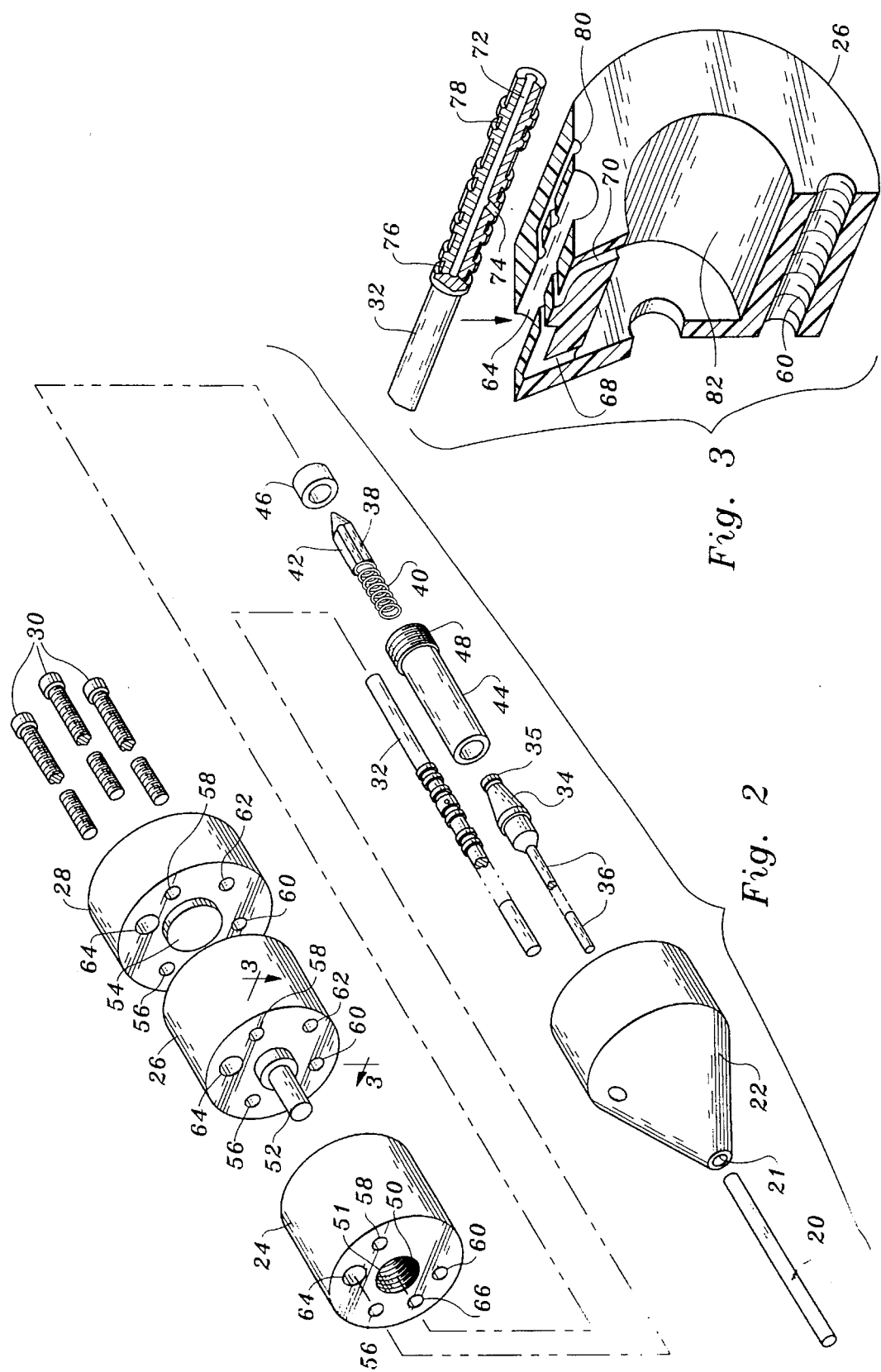

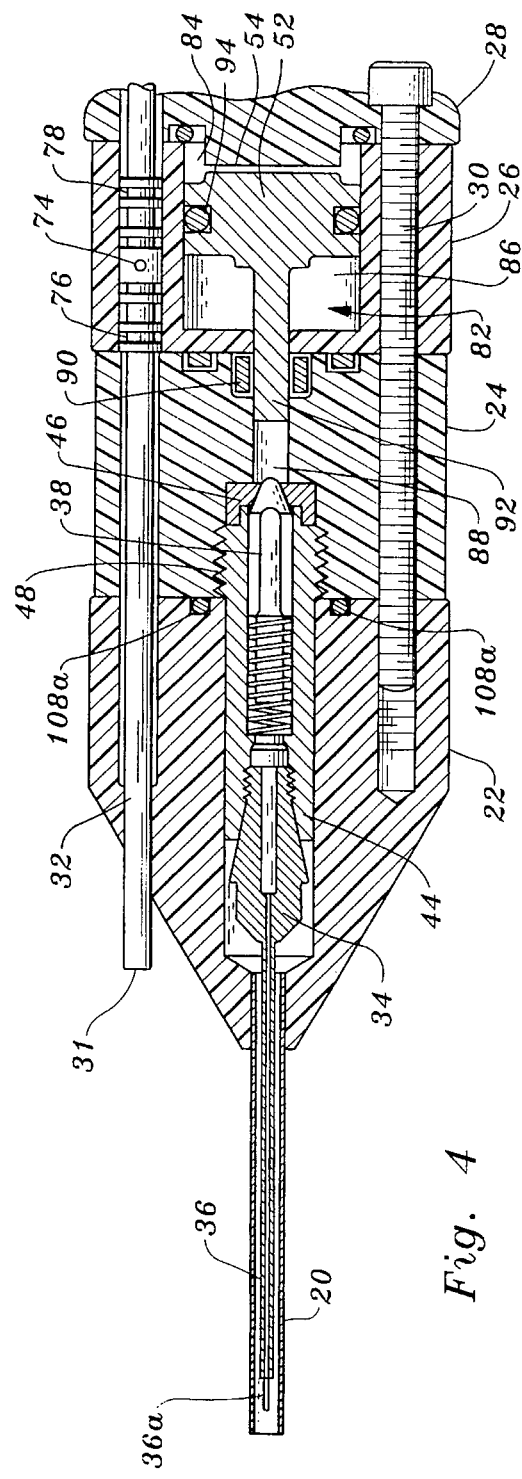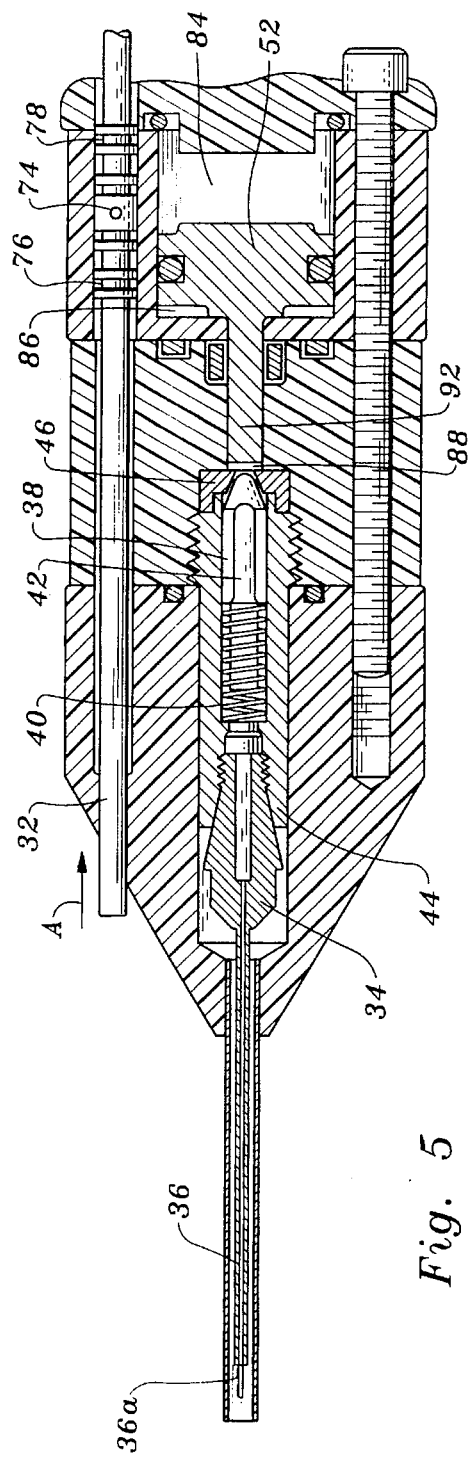
Fig. 4
Fig. 5

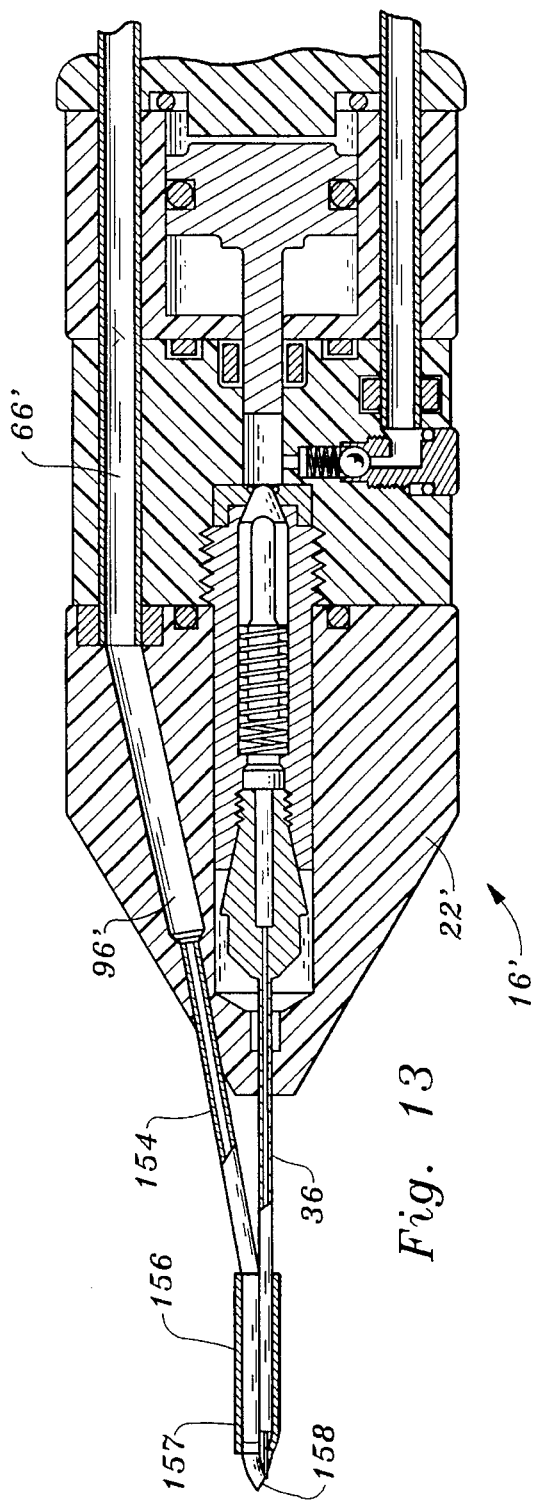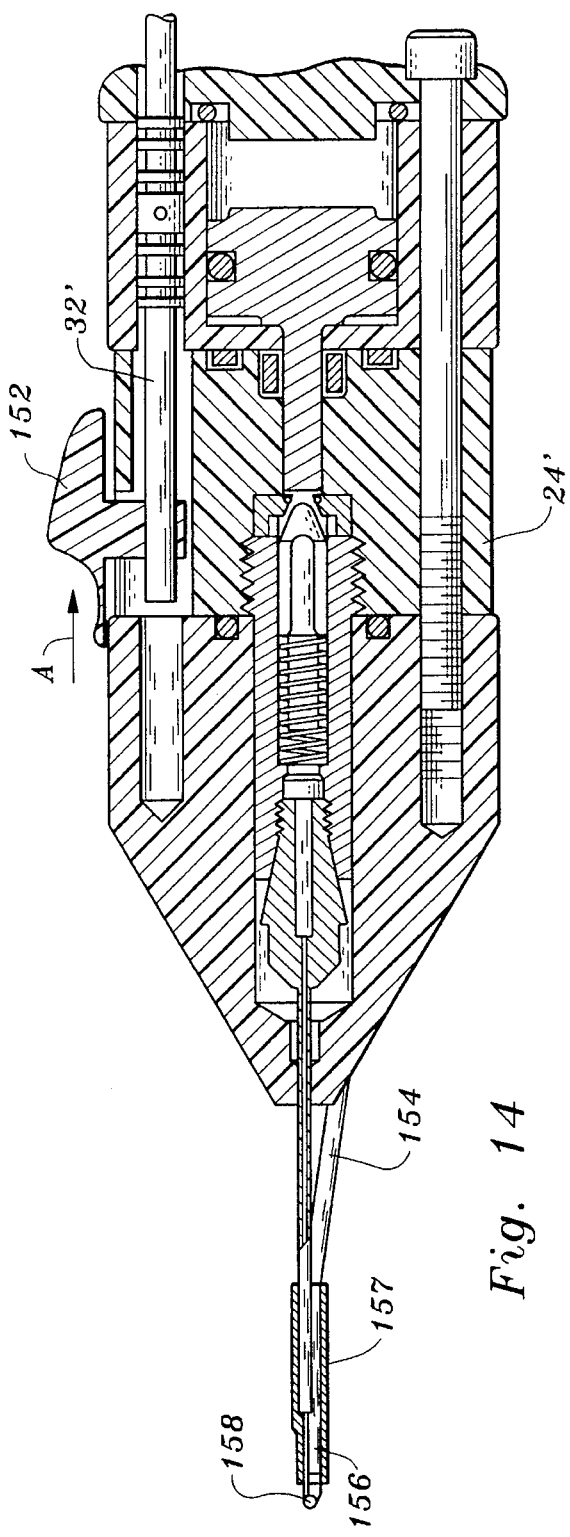

FLUID JET SURGICAL CUTTING INSTRUMENT

BACKGROUND

1. Technical Field

A surgical cutting instrument which employs a fluid jet to cut tissue is provided, where the fluid jet exits the instrument as a high pressure fluid pulse generated from a low pressure fluid input.

2. Background of the Related Art

There has recently been increased interest in the medical community in developing cutting instruments which are highly accurate and which reduce trauma to surrounding tissue to significantly reduce recovery time for the patient. Many new technologies have been utilized in the development of these cutting tools, and as a result there has been increased use of laser tools, electrocautery type tools, ultrasonic emulsification tools, and fluid jets which are very accurate and which allow the surgeon to perform the procedure only on the tissue which is the intended target. However, tools which utilize laser, electrocautery and ultrasonic energy techniques by design generate heat which may in turn cause some damage to surrounding tissue.

On the other hand, fluid jet cutting instruments minimize the potential for damage to surrounding tissue since there is no generation of heat, and the controlled fluid streams may be very localized to permit the surgical procedure to be performed in very close locations. The fluid jet cutters typically are utilized to remove soft tissue, since the fluid jet tends to emulsify soft tissue which is easily removed by aspiration from the surgical site. In particular, fluid jet cutters are utilized in such surgeries as ocular surgery, brain surgery, and other soft tissue surgical procedures. The fluid jet may be controlled by forming discrete pulses, which increases its cutting ability, minimizes the amount of excess fluid present at the surgical site and diminishes the possibility of inadvertent or unintended surgical trauma. As the emulsification of the soft tissue is occurring, it is common to provide an aspiration device which simultaneously removes the excess fluid and emulsified tissue from the surgical site.

However, many of the prior fluid jet cutting devices suffer disadvantages which makes their use a concern to surgeons. In particular, the prior devices generally require external pressurizing sources which provide the instrument with the high pressure fluid jet, so that the curing device is always operating at a high pressure. In addition, many of these devices further require an external or remote pulsing device to provide the fluid pulses at the surgical site. This affords less control to the surgeon, and may also cause an excessive amount of fluid to remain present at the surgical site. Furthermore, unless the pressure is carefully regulated, a steady stream of pulses or a continuous stream of fluid may quickly penetrate into the soft tissue and Cause catastrophic damage. Accordingly, highly skilled personnel must be present during the surgical procedure to perform the cutting procedure with the fluid jet. These prior fluid cutting devices do not inherently prevent high pressure streams or continuous pulses, and must be carefully controlled by the external device and the personnel to avoid serious accidents.

While it is known in some prior devices to provide a pressure generating mechanism in the handle of the instrument itself, these devices generally require a high pressure gas source and a high pressure fluid input which must be carefully regulated by valves and/or pressure relief devices in the instrument itself. Furthermore, these instruments require a large amount of mechanical components, such as springs and check valves to regulate the pressure and provide pulses of fluid at the surgical site.

Therefore, a need exists for a surgical cutting instrument using a fluid jet pulse in which the high pressure fluid pulse is generated in the body of the instrument itself from a low pressure fluid input Furthermore, a need exists for a fluid jet cutting instrument which minimizes the number of mechanical parts to significantly reduce the possibility of mechanical fatigue and failure of the parts. A further need exists for a surgical fluid jet cutting instrument, which utilizes a low pressure gas source to create a high pressure fluid output pulse from a low pressure fluid input.

SUMMARY

A fluid jet cutting instrument is provided which includes a housing having a port for connecting the housing to a low pressure fluid source and a gas source, a cannula extending from the distal end of the housing, a pressure conversion mechanism disposed within the housing which includes a reciprocating piston disposed in an interior cavity within the housing, with the cavity divided by the piston into a drive chamber and a retract chamber. The instrument further includes an actuator for controlling the piston, the actuator including a first passageway for connecting the gas source with the drive chamber and a second passageway for connecting the retract chamber with a vent in the housing to permit the piston to be driven in a distal direction to generate a high pressure fluid output from the distal end of the cannula from the low pressure fluid input.

The actuator also preferably includes a third passageway so that the actuator is movable from an at rest position in which the gas source communicates with the retract chamber through the first passageway and the vent communicates with the drive chamber through the third passageway, to an activated position in which the gas source communicates with the drive chamber through the first passageway and the vent communicates with the retract chamber through the second passageway.

In this manner, the fluid jet cutting instrument minimizes the use of mechanical parts such as springs to return the piston to the at rest position. Instead, the instrument alternates the application of gas pressure to chambers located on either side of the piston head, to utilize the gas source to retract the piston and thus create the fluid output pulse. Thus, a fluid pulse will only be created when the surgeon moves the actuator.

The housing of the apparatus preferably tapers at its distal end to provide a pencil-like body portion which is easily gripped and manipulated by the surgeon during a surgical procedure. The actuator preferably extends through the housing to a position which may be easily manipulated by the surgeon in either a push button or slide button arrangement. Preferably, the connection ports for the fluid source and the gas source are located at the proximal end of the instrument, out of the way when the instrument is being gripped by the surgeon.

The housing itself may be molded or machined to provide a central bore into which the piston and actuator are assembled. Preferably, however, the housing is constructed of at least two sections so that the instrument may be easily assembled and disassembled to replace worn parts or to provide for sterilization.

It is also contemplated that the instrument includes a connection for a suction source, which permits aspiration of excess fluid and emulsified tissue from the surgical site. In one embodiment, the cannula of the instrument comprises a pair of concentric tubes, the inner tube being provided to transport the fluid jet pulse to the surgical site, and the outer tube being provided for suction purposes. Alternately, the suction tube may be provided alongside the jet tube so that the suction tube is substantially parallel to the jet tube. In this embodiment, it is preferred that the opening of the suction tube be positioned so that it is nearly transverse or perpendicular to the fluid jet cutting tube.

The instrument can be used in a variety of surgical procedures. One such application is cataract surgery where the high pressure fluid pulses fracture and emulsify the ocular lens tissue.

BRIEF DESCRIPTION OF THE DRAWINGS

Preferred embodiments of the fluid jet surgical cutting instrument will be described hereinbelow with reference to the drawings, in which:

FIG. 2 illustrates an exploded perspective view of the instrument of FIG. 1;

FIG. 3 illustrates an exploded perspective view of the section of the instrument taken along lines 3—3 of FIG. 2;

FIG. 4 illustrates a side cross-sectional view of the instrument of FIG. 1 in the at rest condition taken along lines 4—4 of FIG. 1;

FIG. 5 illustrates a side cross-sectional view similar to FIG. 4 with the instrument in the operating condition to emit high pressure fluid;

FIG. 13 illustrates a side cross-sectional view of the alternate embodiment of the instrument of FIG. 12 similar to the view taken with respect to FIG. 7;

FIG. 14 illustrates a side cross-sectional view of the instrument of FIG. 12 in a view similar to that shown with respect to FIG. 5, taken along lines 14—14 of FIG. 12;

DETAILED DESCRIPTION OF THE PREFERRED EMBODIMENTS

Figure 1:
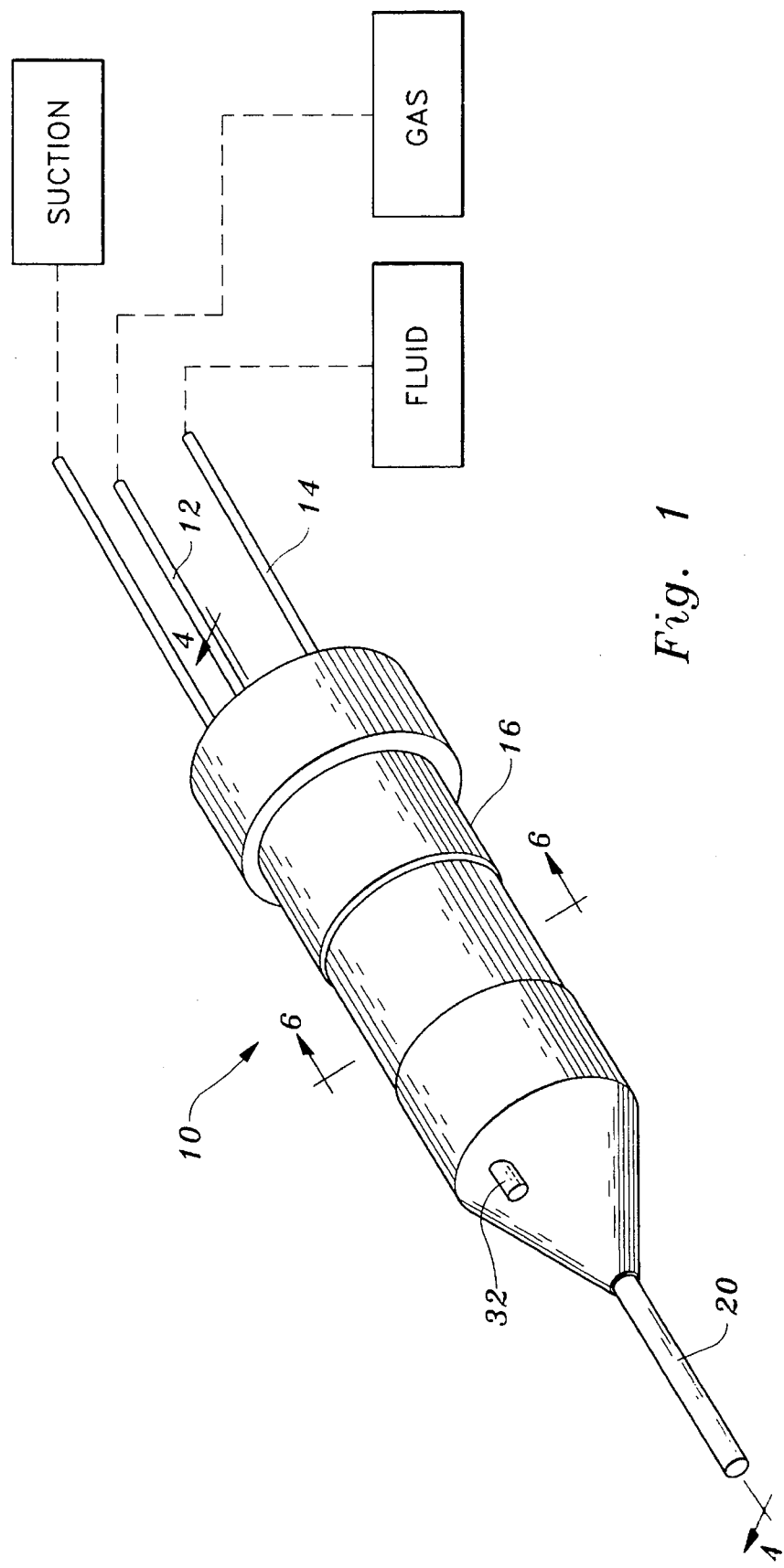
FIG. 1 is a perspective view of the fluid jet surgical cutting instrument.
Figure 6:
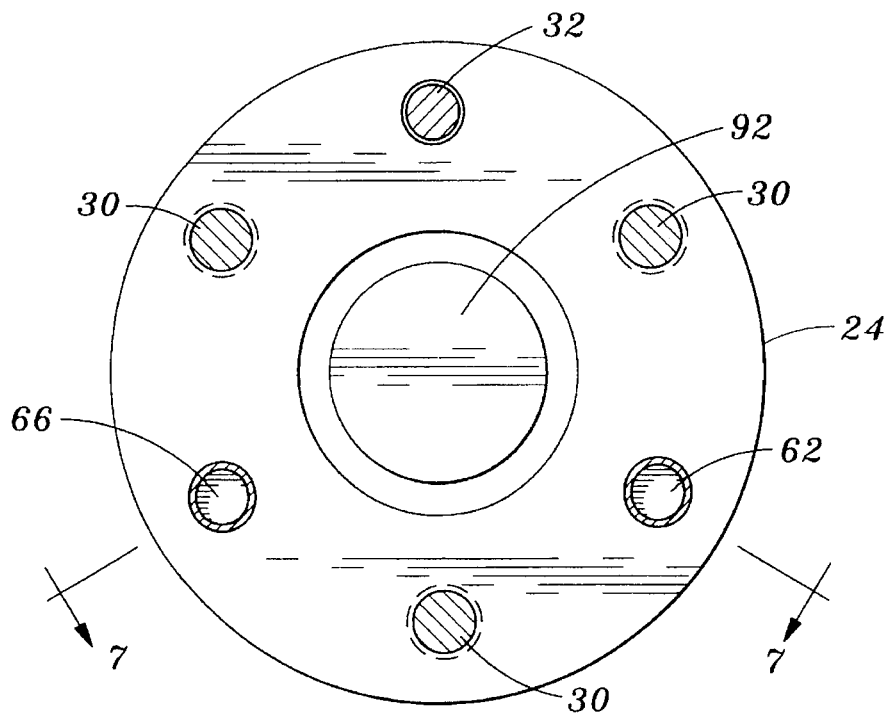
FIG. 6 illustrates a cross-sectional view of the instrument taken along lines 6—6 of FIG. 1.

Referring now to the drawings, in which like reference numerals identify similar or identical elements throughout the several views, FIG. 1 illustrates the fluid jet surgical cutting instrument 10. The instrument includes a housing 16 which is adapted to be gripped by the surgeon and which includes a gas connection 12 and a fluid connection 14 for connection to a gas source and a fluid source, respectively. Instrument 10 is operable through the provision of an actuator 32, extending through housing 16, which when depressed causes a discrete high pressure fluid pulse to exit from cannula 20 in a manner which will be described below. As will become apparent from the discussion below, the instrument 10 converts low pressure fluid input into high pressure fluid output pulses to excise tissue. The high pressure fluid is created by low pressure gas input. This occurs upon movement of actuator 32.

FIG. 2 illustrates the components of instrument 10, which includes a tapered front portion 22, a gas piston chamber housing 26, a pressure amplifier housing 24 and an end cap member 28. Each piece (22, 24, 26, 28) of housing 16 is assembled and held together by screw members 30, three of which are shown as provided in FIG. 2.

Actuator 32 extends through housing 16 and communicates with a series of passageways which permit the introduction of gas and the venting of gas from the gas piston chamber housing 26. Also positioned in the housing 16 is a jet tube housing 34 from which extends jet tube 36 into cannula 20. A tube 36a is telescopically disposed within a distal end of jet tube 36. Jet tube 36 enables proper flow from the fluid chamber to the tube 36a as it provides a smoother transition from the fluid chamber to the smaller diameter tube 36a, thus reducing the pressure drop. Jet tube housing 34 is positioned within a fluid jet assembly housing 44 via screw threads 35 engaging internal threads on housing 44. Housing 44 extends into central opening 51 in housing 24. A pressure relief valve 38 is provided within fluid jet assembly housing 44, which includes a spring member 40 and which further includes fluid passageways 42 whose function will be described below. Spring member 40 is seated over the tip of jet tube housing 34 at which screw threads 35 are located. The fluid jet assembly housing 44 abuts seal member 46 and is secured to pressure amplifier housing 24 at threads 48 which engage internal threads 50 on the housing 24. The proximal end of cannula 20 extends through central opening 21 in front portion 22 and is connected to the suction chamber described below. FIG. 4 shows the positioning of these elements inside the housing 16.

Gas piston chamber housing 26 includes a piston 52 which is configured for reciprocal movement in the interior cavity of gas piston chamber housing 26 via gas pressure. End cap member 28 includes a piston chamber end wall 54 which closes off the interior cavity of gas piston chamber housing 26 as seen in FIG. 4. Piston 52 includes integral piston rod 92 which reciprocates in pressure amplifier housing 24. Screw holes 56, 58 and 60 accommodate the screw members 30 and permit the entire assembly to be properly aligned and assembled. When screw members 30 are properly aligned in the screw holes, aligned holes 62 in housing sections 22, 24, 26 and 28, form fluid passageway 62 which is joined to fluid connection 14, and aligned holes 64 form actuator passageway 64 to receive actuator 32, which is aligned with gas connection 12, in a manner which will be described below. A suction passage 66 formed by aligned holes 66, only one of which is visible in FIG. 2, may also be provided which provides for aspiration capabilities through cannula 20 to remove excess fluid and emulsified tissue from the surgical site.

Figure 10:
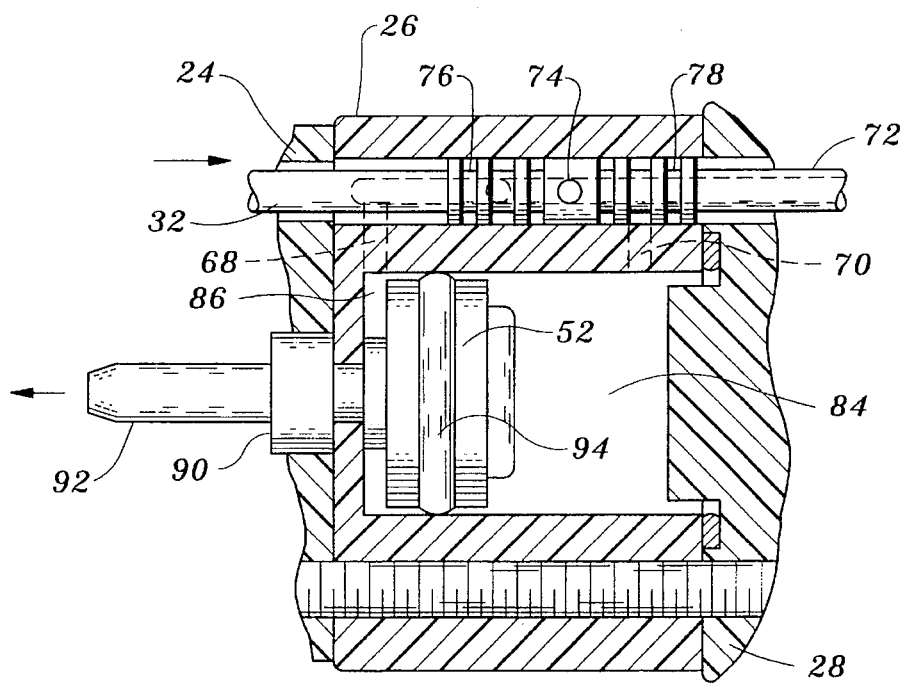
FIG. 10 illustrates a side cross-sectional view of the piston mechanism in the operating condition.
Figure 10A:
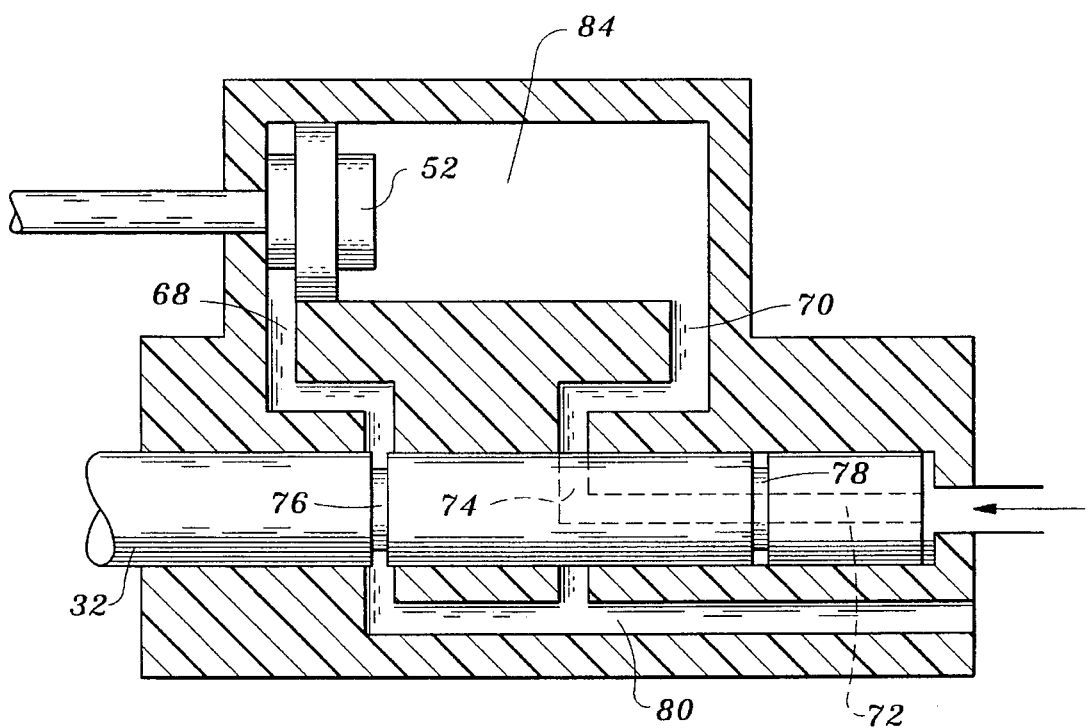
FIG. 10a illustrates a schematic view of the piston and actuator of FIG. 10 in the operating condition.
Figure 11:
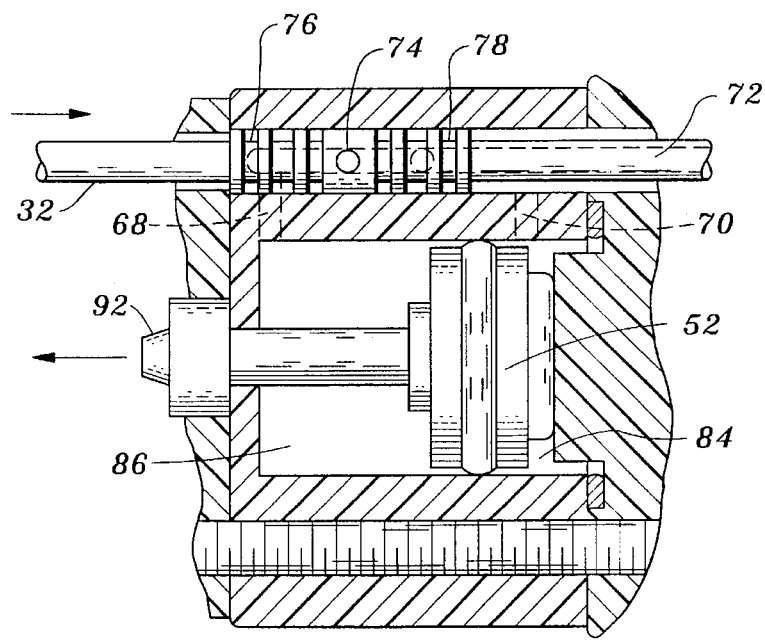
FIG. 11 illustrates a side cross-sectional view of the piston mechanism in the at rest condition.
Figure 11A:
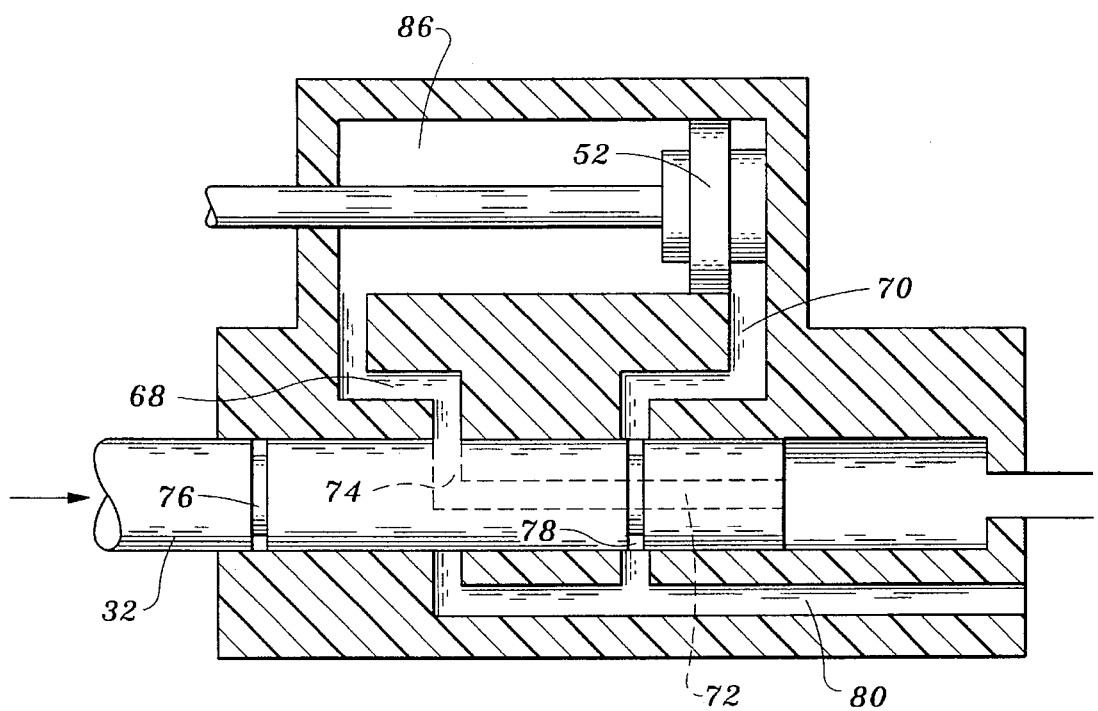
FIG. 11a illustrates a schematic view of the piston and actuator of FIG. 11 in the at rest condition.
Figure 12:
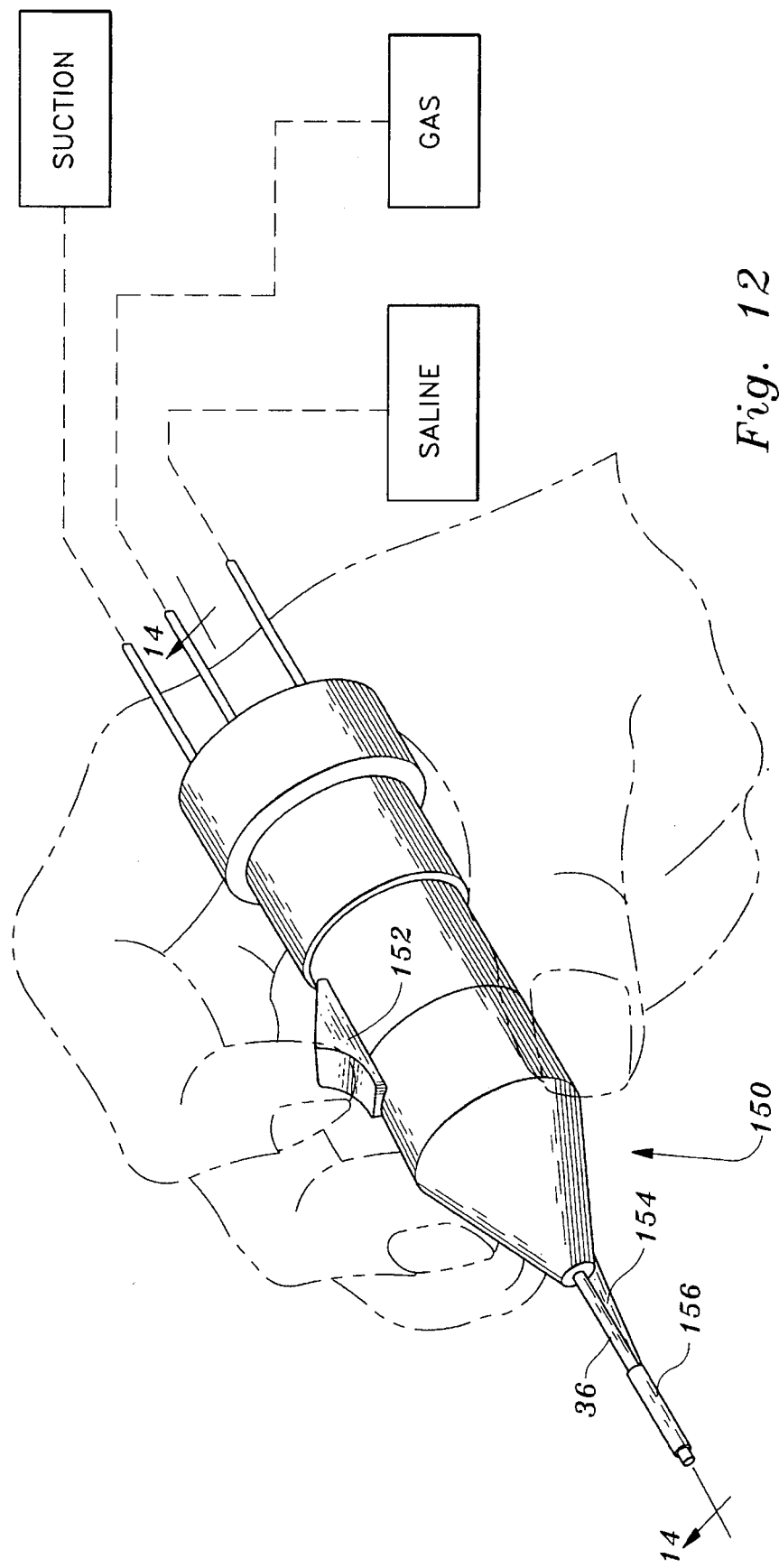
FIG. 12 illustrates a perspective view of an alternate embodiment of the instrument of FIG. 1.
Figure 15:
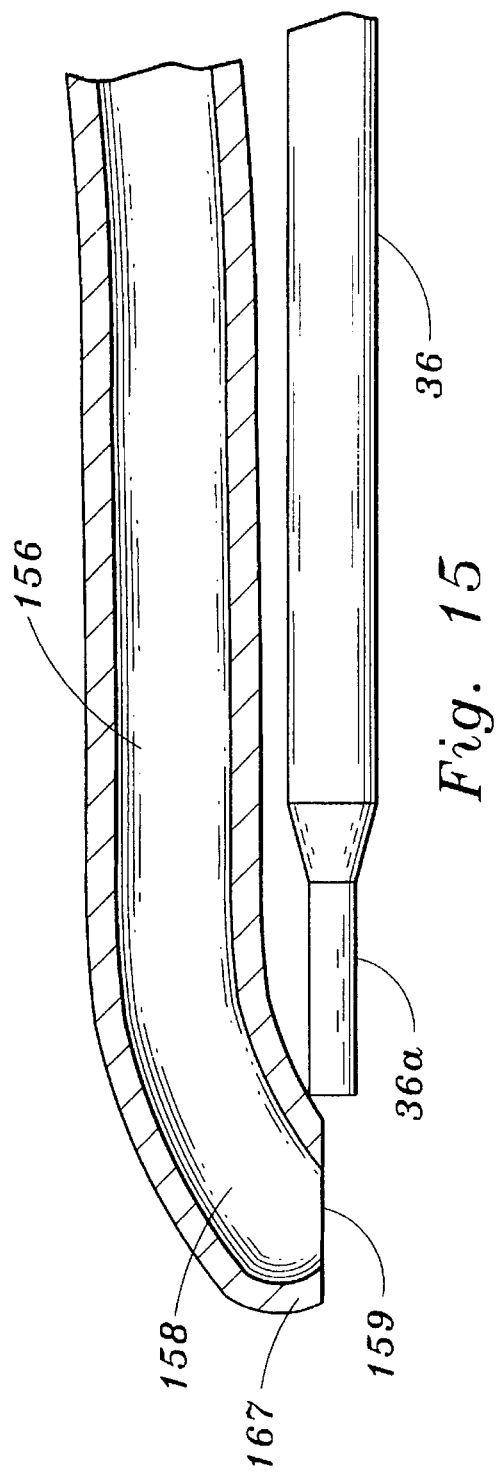
FIG. 15 illustrates an enlarged side view of the distal end of the instrument of FIG. 12.
Figure 16:
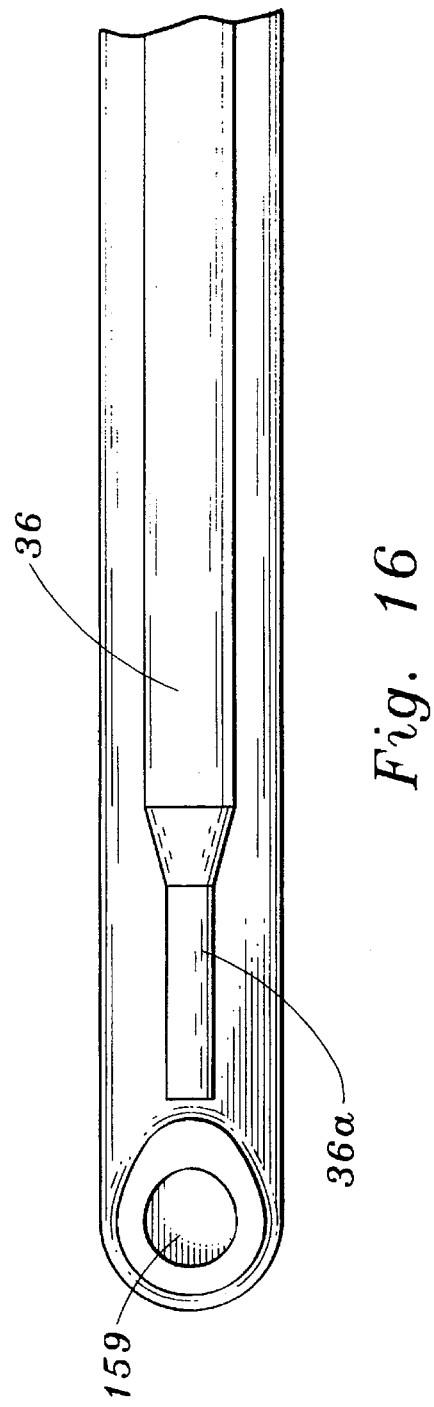
FIG. 16 illustrates a bottom view of the distal end of the instrument of FIG. 12.

Referring now to FIG. 3, it is seen that gas piston chamber housing 26 has an interior cavity which defines a gas piston chamber 82. Actuator 32 is seated in actuator passageway 64, which communicates with exhaust chamber inlet 68, drive chamber inlet 70, and exhaust passageway 80 (see also FIGS. 10a and 11a). Actuator 32 includes a plurality of passageways, and preferably includes a center bore which comprises an actuator first passageway 72 which extends longitudinally and is in communication with the gas connection 12 to supply gas to gas piston chamber 82. Actuator 32 includes a gas port 74 which is in communication with actuator first passageway 72 to supply the gas to gas piston chamber 82 through either of retract chamber inlet 68 or drive chamber inlet 70 depending upon the position of actuator 32. Actuator 32 also includes an actuator second passageway 76 and an actuator third passageway 78 for venting gas piston chamber 82 through exhaust passageway 80. As shown, actuator passageways 76 and 78 are transverse to the elongated first passageway 72 of actuator 32. Actuator 32 is pressure biased to the forward position, i.e., in the direction of cannula 20, by gas pressure. FIG. 11a illustrates the actuator 32 in the distal position (when the instrument is in the rest condition) with actuator third passageway 78 aligned with exhaust passageway 80. FIG. 10a illustrates the actuator 32 in the proximal position (when the instrument is in operating at condition) with actuator second passageway 76 aligned with exhaust passageway 80. This alignment will be discussed in more detail below.

FIG. 4 shows the instrument 10 in the at rest position in which piston member 52 is fully retracted and in a position where it is ready to deliver a fluid pulse through jet tube 36. Actuator 32 is also in the at rest condition i.e. its distal position, awaiting actuation by the surgeon in which the surgeon would apply pressure to the first end 31 of actuator 32 to align the actuator passageways in a manner described below.

As can be seen in FIG. 4, piston 52 includes an O-ring seal member 94 which separates pressure amplifier chamber 82 into drive chamber 84 and retract chamber 86. Piston 52 terminates in reduced diameter piston red 92 which is positioned proximally in fluid chamber 88 in housing 24. Fluid chamber 88 is bounded by piston rod 92 which is sealed by seal member 90 and pressure relief valve 38 which is sealed by seal member 46. Seal member 90 is preferably in the form of a polyethylene seal with a stainless steel energized spring inside. Seal member 46 preferably consists of an orifice which forms a seat for pressure relief valve 38 and a sealing washer composed of nylon.

Figure 7:
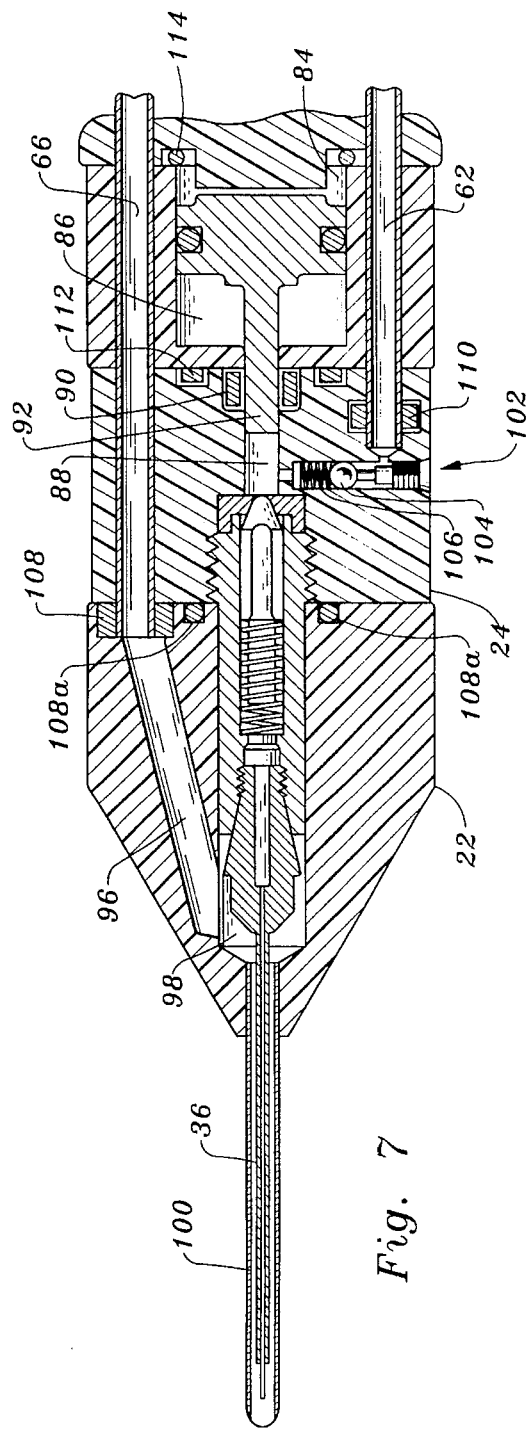
FIG. 7 illustrates a side cross-sectional view of the instrument of FIG. 4 taken along lines 7—7 of FIG. 6 in the at rest condition.

Referring now to FIG. 7, FIG. 7 illustrates the instrument 10 in a different orientation from FIG. 4 which permits a view of the suction passage 66 and the fluid inlet check valve 102 which permits fluid to enter fluid chamber 88 when piston 52 is retracted to the at rest position. Check valve 102 includes a ball 104 and spring 106 (see also FIG. 9), which permits fluid to enter fluid chamber 88 but prevents it from being forced out of fluid chamber 88 through check valve 102. As can be seen in FIGS. 4 and 7, a plurality of seals are provided between the components of the instrument, such as seals 108 and 108a between tapered front portion 22 and pressure amplifier housing 24 at the suction passageway, seal 110 at fluid passageway 62 in housing 24, seal 112 between pressure amplifier housing 24 and gas piston chamber housing 26, and seal 114 between gas piston chamber housing 26 and end cap member 28. In addition, as noted above, seal 90 is provided about piston rod 92 to prevent fluid from leaking past the piston rod 92 as the piston is driven into the fluid chamber 88.

In operation, and once again referring to FIGS. 4 and 7, fluid from fluid passageway 62 enters fluid chamber 88 through check valve 102. When the fluid enters chamber 88, it is bounded by the piston rod 92, the seal 46 and pressure relief valve 38, as well as check valve 102. Piston 52 is in the position shown in FIGS. 4 and 7 where the end of piston 52 abuts the end wall 54, substantially closing off drive chamber 84. In this position, gas supplied to the instrument through gas connection 12 passes through actuator 32 through the provision of actuator first passageway 72 such that it exits gas port 74 into retract chamber inlet 68, as seen in FIGS. 3 and 11a. Retract chamber inlet 68 permits gas to flow into retract Chamber 86 maintaining piston 52 in the position shown in FIG. 4. When actuator 32 is in the position shown in FIG. 4, actuator third passageway 78 is aligned with drive chamber inlet 70 to communicate drive chamber inlet 70 with exhaust passageway 80. This is shown in detail in FIG. 11 and is further schematically shown in FIG. 11a.

In order to operate the instrument 10, actuator 32 is moved in the direction of arrow A as shown in FIG. 5. As seen in FIG. 5, as well as FIG. 8, moving actuator 32 in the direction of arrow A aligns gas port 74 with drive chamber inlet 70 so that gas from gas connection 12 fills drive chamber 84. Simultaneously, actuator second passageway 76 aligns with retract chamber inlet 68, which is further aligned with exhaust passageway 80 permitting gas to escape from retract chamber 86. The sudden rush of gas through drive chamber inlet 70, coupled with the exhaust of gas from retract chamber 86 through exhaust chamber inlet 68, causes the piston 52 to be driven forward towards fluid chamber 88. This is shown in detail in FIG. 10 and is further shown schematically in FIG. 10a.

Figure 9:
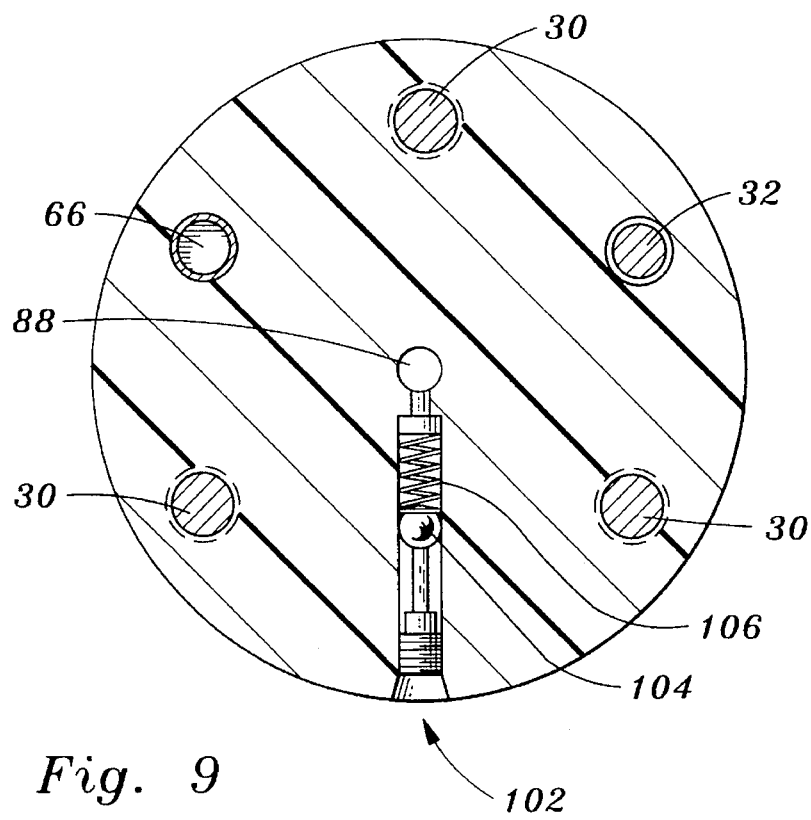
FIG. 9 illustrates a cross-sectional view of the instrument of FIG. 8 taken along lines 9—9 of FIG. 8.
Figure 8:
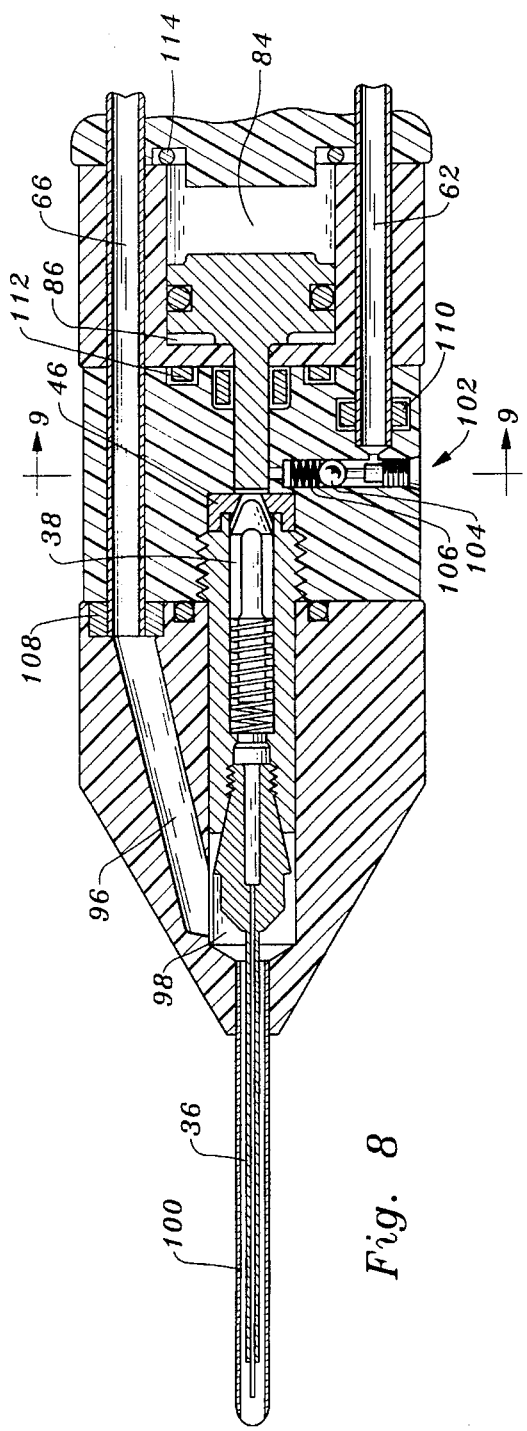
FIG. 8 illustrates the instrument of FIG. 7 with the instrument in the operating condition to emit high pressure fluid.

As the pressure of the fluid accumulates in fluid chamber 88, check valve 102 is closed off, as seen in FIGS. 8 and 9, and the pressure continues to build as the piston is driven to the position shown in FIGS. 5 and 8. Once the pressure in fluid chamber 88 overcomes the value of pressure set by the pressure relief valve 38, valve 38 moves towards the cannula against the biasing of spring 40 to open a passageway for the fluid to escape through seal 46 and around pressure relief valve 38 through the provision of fluid passageway 42. The fluid then exits the jet robe 36 and robe 36a under high pressure to provide a pulse fluid to permit cutting of tissue. The reduced diameter of robe 36a also results in the increase in the fluid pressure at the surgical site.

Once the surgeon releases actuator 32, actuator 32 returns to the position shown in FIG. 4, by realigning gas port 74 with exhaust chamber inlet 68 to permit gas to accumulate in retract chamber 86. Simultaneously, actuator third passageway 78 aligns drive chamber inlet 70 with the exhaust passageway 80 to permit gas to be exhausted from the drive chamber 84 as gas fills the retract chamber 86, driving the piston back to the position shown in FIG. 4. As this occurs, the pressure in fluid chamber 88 is depressed, allowing check valve 102 to open, thus refilling fluid chamber 88 with fluid for the next pulse.

As seen in FIGS. 7 and 8, instrument 10 may also be provided with aspiration capabilities through the provision of suction passageway 66 which communicates which an external suction source. Suction passageway 66 communicates with the angled passageway 96 into suction chamber 98, which further communicates with suction robe 100 formed by cannula 20. As shown, suction robe 100 terminates slightly distally of concentric disposed jet robe 36. The aspiration capabilities permits the surgeon to remove excess fluid and emulsified tissue from the surgical site as it flows in a proximal direction between jet robe 36 and suction robe 100.

FIGS. 12 through 16 illustrate an alternate embodiment of the hand-held fluid jet instrument. Instrument 150 is substantially identical to the embodiment of FIG. 1 except for the provision of an actuator knob 152 for controlling the actuator 32' and a suction tube 154 which joins suction tip 156 at a point adjacent the distalmost tip of the instrument, so that the suction tip 156 extends substantially parallel to the jet tube 36.

Actuator 32' is mounted to actuator knob 152 for longitudinal reciprocal movement to apply high pressure fluid pulses in the manner described above. As shown, actuator knob 152 extends through an opening in fluid chamber housing 24'.

Suction passageway 96' is positioned in front tapered portion 22' of housing 16' and connects suction passageway 66' with suction robe 154. Suction tube 154 extends through an aperture in front tapered portion 22'.

Suction tip 156 extends alongside jet robe 36 and is preferably joined to jet tube 36 at a distal portion through the provision of a robe or heat shrink wrap 157. The distalmost tip 158 is preferably curved so that it is nearly perpendicular to the stream of fluid exiting jet robe 36. The atraumatic curved surface of the distalmost portion (having no sharp radii) prevents the instrument from damaging the anterior or posterior capsule, capsuior rhexos, or other tissue adjacent the surgical site. Tip 158 terminates in a reduced orifice 159. Proximal of the orifice 159, the diameter of the passageway is increased to prevent clogging. The rounded surface and inward curved region 167 which is angled away from the surgical site reduces the possibility of accidentally aspirating posterior capsule or other delicate tissue into the aspiration cannula.

Clogging is also prevented by virtue of the positioning of the suction tip 158 with respect to the jet robe 36, 36a. If a tissue fragment is stock by the orifice 159 and is too large for entry into distalmost suction tip 158, subsequent high pressure fluid pulses will strike the fragment and break it into sufficiently small pieces to enable it to pass into distalmost suction tip 158 and through tip 156 and suction robe 154. The enlarged diameter of the tip 156 and suction robe 154 proximally of suction tip 158 will prevent further clogging since if the fragment is small enough to pass through the orifice, its continued flow through the larger diameter portions will not be obstructed. Thus, the reduced diameter suction inlet orifice 159 is the smallest opening in the aspiration system.

Instrument 150 operates in the same manner as that described above with reference to instrument 10.

The apparatus of FIGS. 1–16 described herein can be used in a variety of surgical procedures. For example, it can be used to remove the lens from the eye capsule in cataract surgery. In this procedure, the distal tip of the cannula is placed adjacent the lens of the eye and pulses of high pressure fluid are controllably applied by movement of actuator 32 or 32'. The high pressure fluid fractures and emulsifies the outer lens tissue, and the excised tissue is removed via the suction passageway. The check valve 38 ensures that only high pressure fluid pluses are emitted. In one embodiment, by way of example, to remove the ocular lens during cataract surgery, Nitrogen is supplied at a pressure between approximately 50 and 200 psi, and preferably at about 160 psi; balanced saline solution (BSS) which provids the cutting fluid is applied at an inlet pressure between about 10 and 100 cm $H_2O$ and preferably about 50 cm $H_2O$; and the BSS cutting pulse jet varies between about 1250 psi (8.6 MPa) and 3750 psi (25.8 MPa), and preferably approximately 2000 psi. Clearly other pressures are contemplated.

Although the subject invention has been described with respect to preferred embodiments, it will be readily apparent to those having ordinary skill in the an to which it appertains that changes and modifications may be made thereto without departing from the spirit or scope of the subject invention as defined by the appended claims.

What is claimed is:

1. A fluid jet surgical cutting instrument comprising:

a housing connectable to a low pressure fluid source and a gas source;

a cannula extending from a distal end of said housing;

a gas pressure driven pressure amplifying mechansim disposed in said housing, said pressure amplifying mechanism including a piston disposed in an interior cavity within said housing, said cavity being divided by said piston into a drive chamber and a retract chamber, said piston being reciprocatingly movable within said cavity; and an actuator for controlling said piston, said actuator including a first passageway situated within said housing for connecting said gas source with said drive chamber, and a second passageway situated within said housing for connecting said retract chamber with an exhaust vent in said housing to permit said piston to be driven in a distal direction to generate a high pressure fluid output from a distal end of said cannula from said low pressure fluid input.

2. A fluid jet surgical cutting instrument according to claim 1, wherein said actuator further includes a third passageway, said actuator being movable from an at rest position in which said gas source communicates with said retract chamber through said first passageway and said vent communicates with said drive chamber through said third passageway, to an activated position in which said gas source communicates with said drive chamber through said first passageway and said vent communicates with said retract chamber through said second passageway.

3. A fluid jet surgical cutting instrument according to claim 2, wherein said actuator is pressure biased to said at rest position, such that said piston reciprocates within said interior cavity upon selective movement of said actuator between said at rest position and said activated position.

4. A fluid jet surgical cutting instrument according to claim 1, further comprising connection means to a source of suction, said suction source being in communication with said cannula.

5. A fluid jet surgical cutting instrument according to claim 4, wherein said cannula comprises a concentric inner tube in communication with said pressure amplifying mechanism, said cannula being in communication with said suction source.

6. A fluid jet surgical cutting instrument according to claim 4, wherein said cannula applies pulsed fluid to a surgical site and a suction tube communicating with said suction source is positioned adjacent said cannula.

7. A fluid jet surgical cutting instrument according to claim 6, wherein a distalmost tip of the suction tube is nearly perpendicular to a distalmost tip of the cannula.

8. A fluid jet surgical cutting instrument according to claim 7, wherein said suction tube has a distal orifice having a diameter less than the diameter of the portion of the suction tube proximal of the orifice.

9. A fluid jet surgical cutting instrument according to claim 1, further comprising a fluid chamber disposed in said housing adjacent said retract chamber, said fluid chamber being in communication with said fluid source and said cannula, said piston being configured to drive said fluid from said fluid chamber out of said cannula.

10. A fluid jet surgical cutting instrument comprising:

a housing including a port for communicating with a low pressure fluid source and a gas source;

a cannula extending from a distal end of said housing;

a gas pressure driven pressure amplifying mechanism disposed in said housing for generating a high pressure fluid output from a low pressure fluid input from said fluid source, said pressure amplifying mechanism including a piston being reciprocatingly movable within an interior cavity of said housing, said interior cavity of said housing being divided by said piston into a drive chamber and a retract chamber; and an actuator for controlling said pressure amplifying mechanism, said actuator being movable within said housing from a first position for supplying gas from said gas source to said drive chamber to drive said piston towards said distal end of said housing, to a second position for supplying gas from said gas source to said retract chamber to drive said piston towards a proximal end of said housing.

11. A fluid jet surgical cutting instrument according to claim 10, wherein said interior cavity of said housing includes a fluid chamber for accommodating low pressure fluid input from said fluid source, said fluid chamber being positioned adjacent said retract chamber and between a distal end of said piston member and said cannula.

12. A fluid jet surgical cutting instrument according to claim 10, wherein said actuator includes a first passageway for connecting said gas source with said drive chamber and a second passageway for connecting said retract chamber with a vent port in said housing when said actuator is in said first position, and a third passageway for connecting said drive chamber with said vent port when said actuator is in said second position.

13. A fluid jet surgical cutting instrument according to claim 12, wherein said first passageway connects said gas source with said retract chamber when said actuator is in said second position.

14. A fluid jet surgical cutting instrument according to claim 13, wherein said actuator is spring biased to said second position by gas pressure.

15. A fluid jet surgical cutting instrument according to claim 11, wherein said drive chamber, said retract chamber and said fluid chamber are sealed from each other, said drive chamber being sealed against said retract chamber, and said retract chamber being sealed against said fluid chamber.

16. A fluid jet surgical cutting instrument according to claim 10, wherein said housing further includes means for connecting said cannula to a suction source.

17. A fluid jet surgical cutting instrument comprising:

a housing including means for connecting said housing to a low pressure fluid source and a gas source, and further including an exhaust port for communicating an interior of said housing with ambient atmosphere;

a cannula extending from an end of said housing;

a gas pressure driven pressure amplifying mechanism disposed in said housing, said pressure amplifying mechanism utilizing said gas source to convert a low pressure fluid into a high pressure fluid output through said cannula; and an actuator for controlling said pressure amplifying mechanism, said actuator including means within said housing for communicating said gas source with said pressure amplifying mechanism, and further including means within said housing for communicating said pressure amplifying mechanism with said exhaust port;

wherein said pressure amplifying mechanism is alternately charged with gas and vented of gas to generate said high pressure fluid output in pulse form.

18. A fluid jet surgical cutting instrument according to claim 17, wherein said pressure amplifying means includes a piston disposed in a cavity in said housing, said piston dividing said cavity into a drive chamber and a retract chamber, said drive chamber and said retract chamber each being selectively communicated with said gas source and said exhaust port through said actuator.

19. A fluid jet surgical cutting instrument according to claim 18, wherein said actuator includes a first passageway in communication with said gas source, and second and third passageways in communication with said exhaust port.

20. A fluid jet surgical cutting instrument according to claim 19, wherein said actuator is movable between an activated position and an at rest position, said first passageway connecting said drive chamber with said gas source and said second passageway connecting said retract chamber with said exhaust port when said actuator is in said activated position, and said first passageway connecting said retract chamber with said gas source and said third passageway connecting said drive chamber with said exhaust port when said actuator is in said at rest position.

21. A fluid jet surgical cutting instrument according to claim 18, further comprising a fluid chamber for receiving a low pressure fluid input from said fluid source, a portion of said piston being positioned within said fluid chamber, such that said piston is movable to drive said low pressure fluid from said fluid chamber out said cannula as a high pressure output.

22. A fluid jet surgical cutting instrument according to claim 20, wherein said actuator is biased to said at rest position.

23. A fluid jet surgical cutting instrument according to claim 17, further comprising means disposed on said housing for connecting said cannula to a source of suction.

\* \* \* \* \*